United States Patent [19]

Jezic

[11] 3,952,028

[45] Apr. 20, 1976

[54] BIS(DICHLOROACETOXY)-IODOBENZENES AND BIS(TRICHLOROACETOXY)IODOBENZENES AND THEIR PREPARATION

[75] Inventor: Zdravko Jezic, Lake Jackson, Tex.

[73] Assignee: The Dow Chemical Company, Midland, Mich.

[22] Filed: July 2, 1974

[21] Appl. No.: 485,179

Related U.S. Application Data

[63] Continuation-in-part of Ser. No. 103,920, Jan. 4, 1971, abandoned.

[52] U.S. Cl. ........................ 260/350 R; 260/453 R; 260/453 R X; 260/479 R; 260/515 A; 260/545 R; 260/612 D; 260/646
[51] Int. Cl.$^2$ ................... C07C 69/00; C07C 71/00
[58] Field of Search ........ 260/350, 453 R, 453 R X, 260/479 R, 515 A, 545 R, 612 D, 646

[56] References Cited
OTHER PUBLICATIONS

Ogata et al., "J.A.C.S.," Vol. 90, pp. 6187–6191 (1960).
Leffler et al., "J.A.C.S.," Vol. 89, pp. 2333–2338 (1959).
Smith, "J. Chem. Soc.," Vol. 1953, pp. 107–109 (1953).

Primary Examiner—Norman Morgenstern
Attorney, Agent, or Firm—Theodore Post; C. Kenneth Bjork

[57] ABSTRACT

Bis(dichloroacetoxy)iodobenzenes and bis(trichloroacetoxy)iodobenzenes corresponding to the formulas

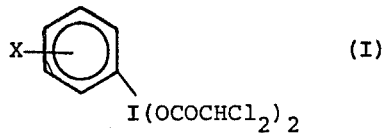

and 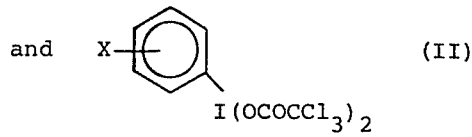

wherein X represents hydrogen, a lower alkyl, a lower alkoxy, a halo, a nitro, a trifluoromethyl, a carboxyl, an amido or a loweralkylcarboxylate group. They are prepared by reacting the corresponding iodosobenzenes with dichloroacetic acid or trichloroacetic acid at substantially room temperature. The compounds are useful as intermediates for the preparation of antimicrobial iodonium salts.

2 Claims, No Drawings

BIS(DICHLOROACETOXY)-IODOBENZENES AND BIS(TRICHLOROACETOXY)IODOBENZENES AND THEIR PREPARATION

This application is a continuation-in-part of U.S. Pat. Application Ser. No. 103,920, filed Jan. 4, 1971, now abandoned.

SUMMARY OF THE INVENTION

The present invention concerns a group of new bis(dichloroacetoxy)iodobenzenes and bis(trichloroacetoxy)iodobenzenes corresponding to the formulas

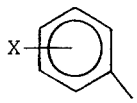 (I) and 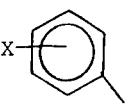 (II)

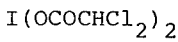 

wherein X represents H, halo (F, Cl or Br), loweralkyl, loweralkoxy, $NO_2$, $CF_3$, $CO_2H$, $CONH_2$ or loweralkylcarboxylate. In the specification and claims, the terms "loweralkyl" and "loweralkoxy" refer to straight and branched chain alkyl and alkoxy groups containing from 1 to 4 carbon atoms, such as, for example, methyl, ethyl, propyl, isopropyl, n-butyl, isobutyl, t-butyl, methoxy, ethoxy, propoxy, isopropoxy, n-butoxy, isobutoxy and t-butoxy. The new compounds are crystalline solids which are substantially insoluble in water and partially soluble in organic solvents such as glacial acetic acid and acetic anhydride. The compounds are useful as intermediates in the preparation of antimicrobially active phenyliodonium salts.

The compounds are prepared by reacting a corresponding iodosobenzene with dichloroacetic acid or trichloroacetic acid according to the following equations:

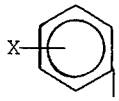  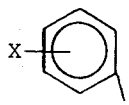 (III A)

 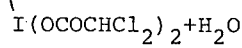

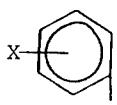  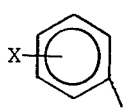 (III B)

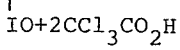 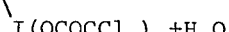

The reaction is advantageously carried out in the presence of a suitable solvent such as, for example, methylene chloride, chloroform, methylchloroform and the like. Also some or all of the solvent can be excess dichloroacetic acid or trichloroacetic acid. The amounts of the reactants to be employed are not critical, some of the product being formed when employing any proportions. The reaction consumes the reactants in the ratio of one mole of the iodosobenzene compound to two moles of the acid, and the employment of such proportions is advantageous. However, superior yields are obtained when using a small excess of the acid reagents. The reaction in each case proceeds at a temperature at which water-of-reaction is liberated, suitably at a temperature of substantially room temperature, for example, between about 15° and about 25°C.

In carrying out the reaction, the iodosobenzene reactant and the acid reactant are contacted in any convenient fashion and maintained for a predetermined period of time in the reaction temperature range to complete the reaction. In a representative procedure, a methylene chloride solution of trichloroacetic acid or dichloroacetic acid is added portionwise to a stirred suspension of the iodosobenzene reactant in methylene chloride. During the addition of the acid reactant to the iodosobenzene reactant and for a period thereafter, the temperature of the reaction mixture is maintained within the reaction temperature range.

Upon completion of the reaction, the desired product is recovered by conventional procedures. To illustrate, the solvent is evaporated under vacuum at a temperature less than about 50°C. or may simply be blown off with air at room temperature and the crude product is washed with a suitable solvent, such as, for example, methylene chloride or ether and air dried or dried in vacuo at room temperature.

DESCRIPTION OF THE PREFERRED EMBODIMENTS

The following examples describe completely representative specific embodiments and the best modes contemplated by the inventor for carrying out the invention.

EXAMPLE I

4-Chloro-bis(trichloroacetoxy)iodobenzene

A quantity of 135 g. (0.53 mole) p-chloroiodosobenzene is suspended in 800 ml. of methylene chloride contained in a 2-liter Erlenmeyer flask. To the suspension is added 190 g. (1.16 mole) trichloroacetic acid dissolved in 500 ml. of methylene chloride with agitation over a 5-minute period, the reaction temperature being maintained at room temperature. After 30 minutes, the solution is filtered and solvent is removed under reduced pressure. The solid residue is triturated with ether and filtered. The solid is collected on the filter, washed with ether and dried. The slightly off-white crystalline solid thereby obtained melts with decomposition at 155°–157°C. The yield is 80–85%. The carbon, hydrogen and iodine analyses and infrared spectra are consistent with the named structure. The substitution of dichloroacetic acid for trichloroacetic acid gives the corresponding 4-chloro-bis(dichloroacetoxy)iodobenzene which melts at 111°–112°C. with decomposition.

EXAMPLE II

Following the procedure of Example I, compounds corresponding to the following formulas are prepared by substituting an equivalent amount of one of the following analogous substituted iodosobenzenes in place of p-chloroiodosobenzene:

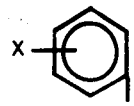

I (TCAO)₂ *

\* (Trichloroacetoxy)₂

I (DCAO)₂ **

\*\* (Dichloroacetoxy)₂

| X | (TCAO)₂ | (DCAO)₂ | Molecular Weight |
|---|---|---|---|
| 4-F | '' | | 546.78 |
| 4-Br | | '' | 538.81 |
| 4-methyl | '' | | 542.82 |
| 4-n-butyl | '' | | 584.89 |
| 4-methoxy | '' | | 558.82 |
| 4-n-butoxy | '' | | 600.89 |
| 4-NO₂ | '' | | 573.79 |
| 3-CF₃ | | '' | 527.90 |
| 4-CO₂H | '' | | 572.80 |
| 4-CONH₂ | '' | | 571.82 |
| 4-CO₂C₂H₅ | | '' | 531.96 |

The compounds of this invention are useful as intermediates in the preparation of antimicrobially-active iodonium trichloro- and dichloro- acetate salts. For such purposes, it is not necessary to separate the preformed bis(trichloroacetoxy) or bis(dichloroacetoxy)iodobenzene from the reaction medium. In fact, it is more convenient to leave the pre-formed bis(trichloroacetoxy) or bis(dichloroacetoxy)iodobenzene in the reaction medium and to add thereto an excess of benzene, loweralkyl benzene, loweralkoxybenzene or thiophene, the excess trichloroacetic acid or dichloroacetic acid acting as condensing agent. In a convenient method for carrying out such reaction, the trichloroacetic acid or dichloroacetic acid and the iodosobenzene reactant are brought together in the reaction medium and the benzene, loweralkylbenzene, loweralkoxybenzene or thiophene is added thereto portionwise with agitation. The reaction is slightly exothermic and goes forward readily with the addition of the said benzene, substituted benzene or thiophene. The temperature of the reaction mixture is controlled by regulating the rate of the addition of the said benzene, substituted benzene or thiophene. The reaction is essentially complete upon completion of the addition of the said benzene, substituted benzene or thiophene. Allowing the reaction mixture to stand for a short period of time at a temperature up to about 50°C. drives the reaction to completion and oftentimes gives some improvement in yield. Upon completion of the reaction, the volatile components of the reaction mixture are distilled off under reduced pressure. The residual oily product crystallizes upon addition of a suitable non-polar solvent such as ether, chloroform, n-hexane or mixtures thereof. By such procedures, compounds such as 4-chlorophenyl-2-thienyliodonium trichloroacetate,
4-chlorophenyl-2-thienyliodonium dichloroacetate,
the corresponding 4-halophenyl phenyliodonium,
4-loweralkylphenyl-2-thienyliodonium,
4-loweralkylphenyl phenyliodonium,
4-loweralkoxyphenyl-2-thienyliodonium,
4-loweralkoxyphenyl phenyliodonium,
4-nitrophenyl-2-thienyliodonium,
4-nitrophenyl phenyliodonium,
3-(trifluoromethyl)phenyl-2-thienyliodonium,
3-(trifluoromethyl)phenyl phenyliodonium,
4-carboxyphenyl-2-thienyliodonium,
4-carboxyphenyl phenyliodonium,
4-carboxamidophenyl-2-thienyliodonium,
4-carboxamidophenyl phenyliodonium,
4-(loweralkylcarboxy)phenyl-2-thienylidonium and,
4-(loweralkylcarboxy)phenyl phenyliodonium trichloroacetate and dichloroacetate salts are prepared from the intermediates of this invention.

The said phenyl-thienyliodonium trichloro- and dichloro- acetate salts, prepared from the bis(trichloroacetoxy)iodobenzenes and bis(dichloroacetoxy)iodobenzenes of this invention, give 100 percent kills against Staphylococcus aureus and Salmonella typhosa at about 0.001 percent by weight concentration in nutrient agar inoculated with the said organisms, while the corresponding said phenyl phenyliodonium trichloro- and dichloro- acetate salts, similarly prepared from the intermediates of this invention, give 100 percent kills against Staphylococcus aureus and Salmonella typhosa at concentrations varying from about 0.010 to 0.050 percent when similarly tested.

The iodosobenzene starting materials are prepared in ways disclosed by Banks, Chemical Reviews 66, 245 (1966); Beringer et al., J.A.C.S. 81, 345 (1959); and Iodine Abstracts and Reviews, Vol. 3, No. 3, 2–70 (1956).

What is claimed is:
1. A compound represented by the formula

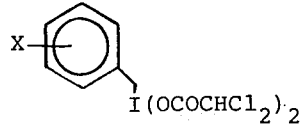

I(OCOCHCl₂)₂ or

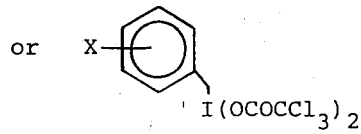

I(OCOCCl₃)₂ wherein X represents H, F, Cl, Br, loweralkyl, loweralkoxy, NO₂, CF₃, CO₂H, CONH₂ or loweralkylcarboxylate.

2. The compound of claim 1 wherein X represents 4-chloro.

* * * * *